(12) United States Patent
Relan et al.

(10) Patent No.: US 11,229,393 B2
(45) Date of Patent: *Jan. 25, 2022

(54) METHODS AND SYSTEMS FOR STATISTICALLY ANALYZING ELECTROGRAMS FOR LOCAL ABNORMAL VENTRICULAR ACTIVITIES AND MAPPING THE SAME

(71) Applicant: St. Jude Medical, Cardiology Division, Inc., St. Paul, MN (US)

(72) Inventors: Jatin Surendra Relan, Bordeaux (FR); Pierre Jais, Pessac (FR)

(73) Assignee: ST. JUDE MEDICAL, CARDIOLOGY DIVISION, INC., St. Paul, MN (US)

( * ) Notice: Subject to any disclaimer, the term of this patent is extended or adjusted under 35 U.S.C. 154(b) by 198 days.

This patent is subject to a terminal disclaimer.

(21) Appl. No.: 16/545,233

(22) Filed: Aug. 20, 2019

(65) Prior Publication Data

US 2020/0046238 A1    Feb. 13, 2020

Related U.S. Application Data

(63) Continuation of application No. 15/367,895, filed on Dec. 2, 2016, now Pat. No. 10,398,331.

(Continued)

(51) Int. Cl.
*A61B 5/349* (2021.01)
*G16H 50/20* (2018.01)
(Continued)

(52) U.S. Cl.
CPC .............. *A61B 5/349* (2021.01); *A61B 5/316* (2021.01); *A61B 5/339* (2021.01); *A61B 5/347* (2021.01);
(Continued)

(58) Field of Classification Search
None
See application file for complete search history.

(56) References Cited

U.S. PATENT DOCUMENTS 5,697,377 A    12/1997    Wittkampf
5,983,126 A    11/1999    Wittkampf
(Continued)

FOREIGN PATENT DOCUMENTS

EP    2901953    8/2015
JP    2015-139707    8/2015
WO    2010/054409    5/2010

OTHER PUBLICATIONS

Sacher, Frederic et al., Substrate Mapping and Ablation for Ventricular Tachycardia: The LAVA Approach, Apr. 2015, vol. 26, No. 4, pp. 464-471.

(Continued)

*Primary Examiner* — Kennedy Schaetzle
(74) *Attorney, Agent, or Firm* — Wiley Rein LLP (57) ABSTRACT

Cardiac activity (e.g., a cardiac electrogram) is analyzed for local abnormal ventricular activity (LAVA), such as by using a LAVA detection and analysis module incorporated into an electroanatomical mapping system. The module transforms the electrogram signal into the wavelet domain to compute as scalogram; computes a one-dimensional LAVA function of the scalogram; detects one or more peaks in the LAVA function; and computes a peak-to-peak amplitude of the electrogram signal. If the peak-to-peak amplitude does not exceed a preset amplitude threshold, then the module can compute one or more of a LAVA lateness parameter for the electrogram signal using one of the one or more peaks detected in the LAVA function and a LAVA probability parameter for the electrogram signal.

18 Claims, 9 Drawing Sheets

Related U.S. Application Data (60) Provisional application No. 62/330,886, filed on May 3, 2016, provisional application No. 62/263,136, filed on Dec. 4, 2015.

(51) Int. Cl.

| | | |
|---|---|---|
| *A61B 5/00* | (2006.01) | |
| *A61B 5/316* | (2021.01) | |
| *A61B 5/339* | (2021.01) | |
| *A61B 5/352* | (2021.01) | |
| *A61B 5/361* | (2021.01) | |
| *A61B 5/363* | (2021.01) | |
| *A61B 5/364* | (2021.01) | |
| *A61B 5/366* | (2021.01) | |
| *A61B 5/347* | (2021.01) | |

(52) U.S. Cl.
CPC .............. *A61B 5/352* (2021.01); *A61B 5/361* (2021.01); *A61B 5/363* (2021.01); *A61B 5/364* (2021.01); *A61B 5/366* (2021.01); *A61B 5/726* (2013.01); *A61B 5/7264* (2013.01); *G16H 50/20* (2018.01); *A61B 5/6852* (2013.01); *A61B 5/7275* (2013.01); *A61B 2505/05* (2013.01)

(56) References Cited

U.S. PATENT DOCUMENTS

| | | | |
|---|---|---|---|
| 6,640,119 B1 | 10/2003 | Budd et al. | |
| 6,728,562 B1 | 4/2004 | Budd et al. | |
| 6,939,309 B1 | 9/2005 | Beatty et al. | |
| 6,947,785 B1 | 9/2005 | Beatty et al. | |
| 6,978,168 B2 | 12/2005 | Beatty et al. | |
| 6,990,370 B1 | 1/2006 | Beatty et al. | |
| 7,263,397 B2 | 8/2007 | Hauck et al. | |
| 7,885,707 B2 | 2/2011 | Hauck | |
| 8,812,091 B1 | 8/2014 | Brodnick | |
| 9,332,920 B2 | 5/2016 | Thakur et al. | |
| 9,662,178 B2 | 5/2017 | Nanthakumar et al. | |
| 9,706,935 B2 | 7/2017 | Spector | |
| 9,888,862 B2 | 2/2018 | Harlev et al. | |
| 10,398,331 B2 * | 9/2019 | Relan | A61B 5/361 |
| 2004/0193065 A1 | 9/2004 | Houben | |
| 2007/0167706 A1 | 7/2007 | Boese et al. | |
| 2007/0287902 A1 | 12/2007 | Fuimaono et al. | |
| 2010/0249627 A1 | 9/2010 | Zhang et al. | |
| 2011/0019892 A1 | 1/2011 | Rahn et al. | |
| 2012/0165684 A1 | 6/2012 | Sholder | |
| 2014/0180051 A1 | 6/2014 | Thakur et al. | |
| 2015/0009992 A1 | 1/2015 | Zhang | |
| 2015/0032016 A1 | 1/2015 | Ghosh | |
| 2015/0157267 A1 | 6/2015 | Shushan et al. | |
| 2015/0228254 A1 | 8/2015 | Olson | |
| 2016/0128785 A1 | 5/2016 | Nanthakumar et al. | |
| 2017/0105680 A1 | 4/2017 | Shushan et al. | |
| 2017/0367603 A1 | 12/2017 | Spector | |
| 2018/0137687 A1 | 5/2018 | Katz et al. | |

OTHER PUBLICATIONS

Komatsu Yuki et al., Electrophysiologic Characterization of Local Abnormal Ventricular Activities in Postinfarction Ventricular Tachycardia with Respect to Their Anatomic Location, Heart Rhythm Society, Aug. 20, 2013, vol. 10, No. 11, pp. 1630-1637.

Houben, Richard P.M., Analysis of Fractionated Atrial Fibrillation Electrograms by Wavelet Decomposition, IEEE Transactions on Biomedical Engineering, Jun. 6, 2010, vol. 57, No. 6, pp. 1388-1398.

Eklund et al., Medical Image Processing on the GPU: Past, Present and Future, May 2013, Medical Image Analysis.

* cited by examiner

METHODS AND SYSTEMS FOR STATISTICALLY ANALYZING ELECTROGRAMS FOR LOCAL ABNORMAL VENTRICULAR ACTIVITIES AND MAPPING THE SAME

CROSS-REFERENCE TO RELATED APPLICATIONS

This application is a continuation of U.S. application Ser. No. 15/367,895, filed 2 Dec. 2016 ("the '895 application"), now U.S. Pat. No. 10,398,331, which claims the benefit of U.S. provisional application No. 62/263,136, filed 4 Dec. 2015 ("the '136 application"), and U.S. provisional application No. 62/330,886, filed 3 May 2016 ("the '886 application"). The foregoing are hereby incorporated by reference as though fully set forth herein.

BACKGROUND

The present disclosure relates generally to electrogram detection and analysis, such as may be performed in cardiac diagnostic and therapeutic procedures. More specifically, the present disclosure relates to a system and method for detecting, analyzing, and mapping Local Abnormal Ventricular Activities (LAVA) from electrogram data.

In Ventricular Tachycardia (VT) formation, Local Abnormal Ventricular Activities (LAVAs) represent surviving potentials from slow conducting channels within a scar. These LAVAs are present due to trapping of the depolarization wave along a slow, highly fibrotic conducting channel present within a dense scar. These trapped LAVAs usually have multiple entry and exit points to trigger a macroscopic re-entry, thus causing VT.

Figure 1A:
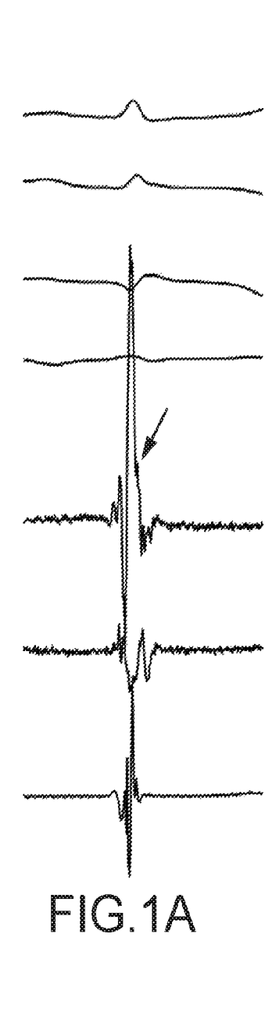
FIGS. 1A-1E are several views of exemplary electrogram signals showing the presence of early and late LAVAs.
Figures 1B, 1C:
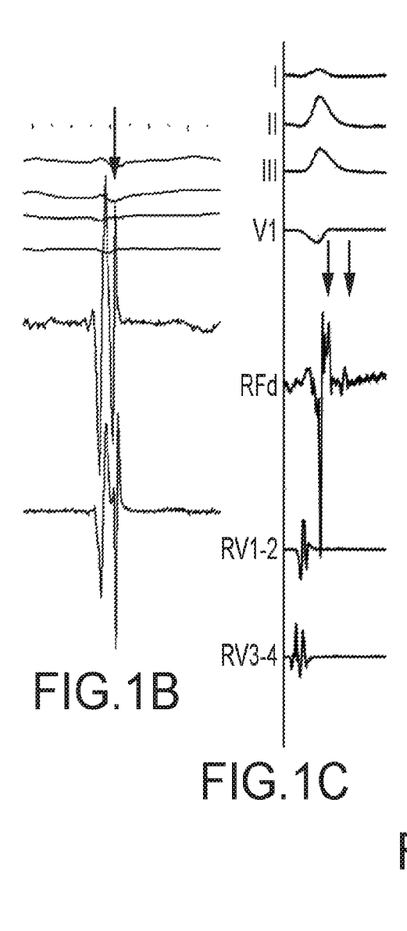
Figure 1D:
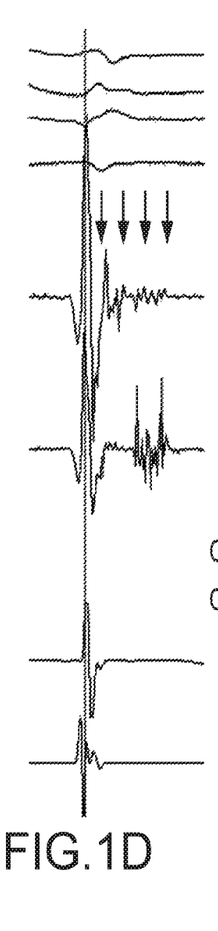
Figure 1E:
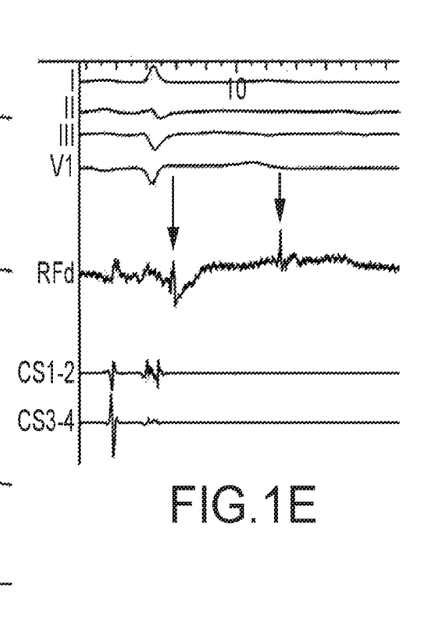

Substrate-based approaches for detecting LAVAs target delayed signals relative to the detected QRS-complex within the signal, which are often defined as late-potentials. Such approaches may miss a significant proportion of LAVA, however, particularly in the septum and other early-to-activate regions. This can be seen in the exemplary electrogram signals depicted in FIGS. 1A-1E. FIGS. 1A-1C, for example, depict the presence of early LAVAs fused and buried within the EGM QRS portion of the signal whereas FIGS. 1D-1E depict late LAVAs that are more observable on the lateral or epicardial side of the heart. It is hypothesized that elimination of LAVAs recorded during sinus rhythm or ventricular pacing would be feasible as an end point for VT ablation, and that complete elimination of LAVAs would lead to an increase in arrhythmia-free survival. Currently during an EP study, these LAVAs are manually tagged by EP physicians based on certain bipolar electrogram (EGM) characteristics. This manual annotation process can be quite tedious and difficult for the physician to perform, particularly for high density electrograms.

BRIEF SUMMARY

Disclosed herein is a method of analyzing cardiac activity for local abnormal ventricular activity (LAVA), including the steps of receiving an electrogram signal at a signal processor; and using the signal processor: transforming the electrogram signal into the wavelet domain, thereby computing a scalogram; computing a one-dimensional LAVA function of the scalogram; detecting one or more peaks in the LAVA function; computing a peak-to-peak amplitude of the electrogram signal, and, if the peak-to-peak amplitude does not exceed a preset amplitude threshold: computing a LAVA lateness parameter for the electrogram signal using one of the one or more peaks detected in the LAVA function; and computing a LAVA probability parameter for the electrogram signal. The electrogram signal can be transformed into the wavelet domain by applying a continuous wavelet transformation to the electrogram signal to compute the scalogram.

It is contemplated that values of the scalogram less than a preset noise threshold, such as about 0.2, can be set to zero.

According to aspects of the disclosure, the step of computing a one-dimensional LAVA function of the scalogram can include computing a one-dimensional LAVA function of the scalogram at a preset cardiac activity frequency, such as about 300 Hz.

In embodiments, the step of detecting one or more peaks in the LAVA function includes: detecting one or more dominant activity peaks in the LAVA function; and categorizing each dominant activity peak of one or more dominant activity peaks as a near-field peak, a far-field peak, or a noise peak. Dominant activity peaks can be detected in the LAVA function by detecting one or more local maximum peaks in the LAVA function where a maximum value of a slope of the electrogram signal exceeds a preset discrete activity threshold, such as about 0.2 mV/msec, within a preset refractory window surrounding the local maximum peak. A dominant peak can be categorized as a near-field peak if the LAVA function exceeds a preset near field threshold at the dominant activity peak, as a far-field peak if the LAVA function exceeds a preset far field threshold and not the preset near field threshold at the dominant activity peak, and as a noise peak otherwise.

The LAVA lateness parameter can be computed as a time difference between: a latest far-field peak of the one or more peaks detected in the LAVA function and a reference ECG QRS, if the one or more peaks detected in the LAVA function do not include any near-field peaks; and a latest near-field peak of the one or more peaks detected in the LAVA function and the reference ECG QRS if the one or more peaks detected in the LAVA function do include at least one near-field peak.

The LAVA probability parameter can be computed using one or more of: the LAVA lateness parameter for the electrogram signal; a fractionation parameter for the electrogram signal; a number of peaks detected in the LAVA function; a number of far-field peaks detected in the LAVA function; a near field activity span for the electrogram signal; a number of isolated QRS activities for the electrogram signal; and a QRS activity duration for the electrogram signal. According to aspects of the disclosure, the fractionation parameter for the electrogram signal is computed as a number of sign changes in a slope of the electrogram signal between an earliest near-field peak detected in the LAVA function and a latest near-field peak detected in the LAVA function. According to other aspects of the disclosure, the fractionation parameter for the electrogram signal is computed as a number of sign changes in a slope of the electrogram signal, after the electrogram signal has been filtered to remove noise, between an earliest near-field peak detected in the LAVA function and a latest near-field peak detected in the LAVA function. It is also contemplated that the QRS activity duration for the electrogram signal can be computed using the one or more peaks detected in the LAVA function.

The method can also include generating a graphical representation of one or more of the LAVA lateness parameter and the LAVA probability parameter on a cardiac model.

Also disclosed herein is a method of analyzing a cardiac electrogram for local abnormal ventricular activity (LAVA) in an electroanatomical mapping system. The method includes the electroanatomical mapping system: transforming the cardiac electrogram into the wavelet domain, thereby computing a scalogram; computing a one-dimensional LAVA function of the scalogram; detecting one or more peaks in the LAVA function; computing a peak-to-peak amplitude of the electrogram signal, and, if the peak-to-peak amplitude does not exceed a preset amplitude threshold, computing at least one of: a LAVA lateness parameter for the electrogram signal using one of the one or more peaks detected in the LAVA function; and a LAVA probability parameter for the electrogram signal.

According to aspects of the instant disclosure, the step of detecting one or more peaks in the LAVA function includes detecting one or more local maximum peaks in the LAVA function where a maximum value of a slope of the electrogram signal exceeds a preset discrete activity threshold within a preset refractory window surrounding the local maximum peak; and the LAVA function exceeds at least a preset far field threshold at the local maximum peak.

The method can also include generating a graphical representation of the at least one of the LAVA lateness parameter and the LAVA probability parameter on a cardiac model.

The instant disclosure also provides an electroanatomical mapping system configured to analyze an electrogram signal for local abnormal ventricular activity (LAVA). The system includes: a LAVA analysis processor configured to: transform the electrogram signal into the wavelet domain, thereby computing a scalogram; compute a one-dimensional LAVA function of the scalogram; detect one or more peaks in the LAVA function; and compute one or more of a LAVA lateness parameter for the electrogram signal using one of the one or more peaks detected in the LAVA function and a LAVA probability parameter for the electrogram signal. The LAVA analysis processor can further be configured to compute the one or more of the LAVA lateness parameter and the LAVA probability parameter when a peak-to-peak amplitude of the electrogram signal does not exceed a preset amplitude threshold. The system can also include a mapping processor configured to generate a graphical representation of the one or more of the LAVA lateness parameter and the LAVA probability parameter on a cardiac model.

The foregoing and other aspects, features, details, utilities, and advantages of the present invention will be apparent from reading the following description and claims, and from reviewing the accompanying drawings.

While multiple embodiments are disclosed, still other embodiments of the present disclosure will become apparent to those skilled in the art from the following detailed description, which shows and describes illustrative embodiments. Accordingly, the drawings and detailed description are to be regarded as illustrative in nature and not restrictive.

DETAILED DESCRIPTION

The present disclosure relates to systems and methods to automatically detect sharp fractionated, near-field activity peaks and relatively less sharp far-field activity peaks within a bipolar electrogram (EGM), and from this information assign various metrics to the EGM, including the probability that the signal includes one or more Local Abnormal Ventricular Activities (LAVAs), and a lateness of the last near-field activity detected relative to a surface ECG QRS. From these metrics, a LAVA probability map and LAVA lateness map can be generated and displayed using an EP mapping system (e.g., using a electroanatomical mapping system such as the ENSITE VELOCITY system from St. Jude Medical).

LAVAs may be defined as sharp fractionated bi-polar potentials (with significant slope (dv/dt) representing the local near-field activity) appearing at any time during or after the far-field EGM. While these potentials may be separated from the far-field portion of the signal by an isoelectric line and often extend beyond the end of surface QRS, they may also appear fused or buried within the QRS, as can be seen, for example, in FIGS. 1A-1C. Lateness of LAVA may be defined as the timing difference between the onset of surface QRS to the last detected LAVA potential. Lateness of LAVA is affected to a large extent by their spatial locations. The chance of detecting late LAVAs increases when the electrogram onset is later.

Figure 2:
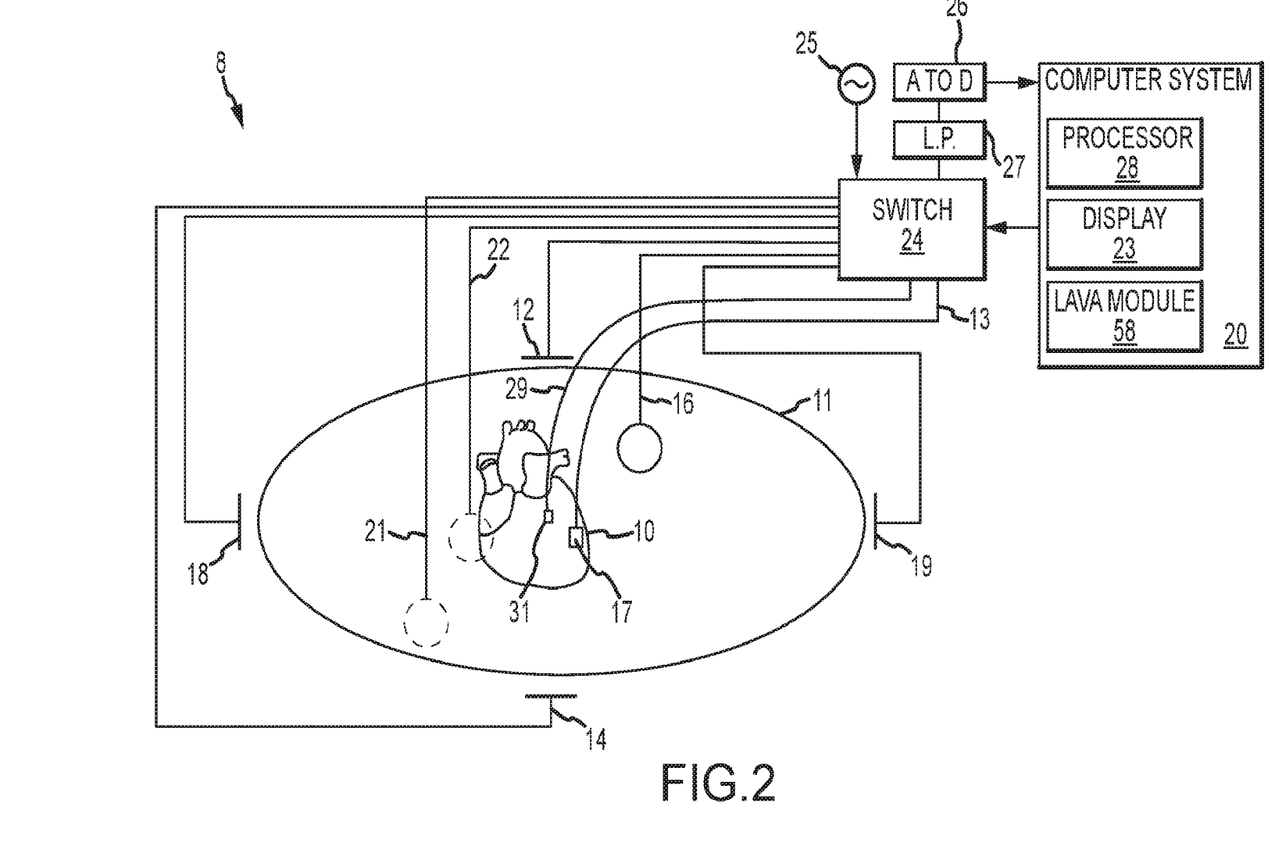
FIG. 2 is a schematic diagram of an exemplary electroanatomical mapping system, such as may be used to detect and analyze electrogram signals containing LAVAs.

FIG. 2 shows a schematic diagram of an exemplary system 8 for conducting cardiac electrophysiology studies by navigating a cardiac catheter and measuring electrical activity occurring in a heart 10 of a patient 11 and three-dimensionally mapping the electrical activity and/or information related to or representative of the electrical activity so measured. System 8 can be used, for example, to create an anatomical model of the patient's heart 10 using one or more electrodes. System 8 can also be used to measure electrophysiology data at a plurality of points along a cardiac surface and store the measured data in association with location information for each measurement point at which the electrophysiology data was measured, for example to create a diagnostic data map of the patient's heart 10. In some embodiments, and as discussed further herein, the system 8 can be used to generate electrophysiology maps containing various metrics associated with late activations. In some embodiments, for example, the system 8 includes various software and hardware functionality to aid in detecting the probability of LAVAs existing in a bipolar EGM signal. The system 8 may also be used to compute various other metrics associated with LAVAs, as further discussed herein.

As one of ordinary skill in the art will recognize, and as will be further described below, system 8 determines the location, and in some aspects the orientation, of objects, typically within a three-dimensional space, and expresses those locations as position information determined relative to at least one reference.

For simplicity of illustration, the patient 11 is depicted schematically as an oval. In the embodiment shown in FIG. 2, three sets of surface electrodes (e.g., patch electrodes) are shown applied to a surface of the patient 11, defining three generally orthogonal axes, referred to herein as an x-axis, a y-axis, and a z-axis. In other embodiments the electrodes could be positioned in other arrangements, for example multiple electrodes on a particular body surface. As a further alternative, the electrodes do not need to be on the body surface, but could be positioned internally to the body.

In FIG. 2, the x-axis surface electrodes 12, 14 are applied to the patient along a first axis, such as on the lateral sides of the thorax region of the patient (e.g., applied to the patient's skin underneath each arm) and may be referred to as the Left and Right electrodes. The y-axis electrodes 18, 19 are applied to the patient along a second axis generally orthogonal to the x-axis, such as along the inner thigh and neck regions of the patient, and may be referred to as the Left Leg and Neck electrodes. The z-axis electrodes 16, 22 are applied along a third axis generally orthogonal to both the x-axis and the y-axis, such as along the sternum and spine of the patient in the thorax region, and may be referred to as the Chest and Back electrodes. The heart 10 lies between these pairs of surface electrodes 12/14, 18/19, and 16/22.

An additional surface reference electrode (e.g., a "belly patch") 21 provides a reference and/or ground electrode for the system 8. The belly patch electrode 21 may be an alternative to a fixed intra-cardiac electrode 31, described in further detail below. It should also be appreciated that, in addition, the patient 11 may have most or all of the conventional electrocardiogram ("ECG" or "EKG") system leads in place. In certain embodiments, for example, a standard set of 12 ECG leads may be utilized for sensing electrocardiograms on the patient's heart 10. This ECG information is available to the system 8 (e.g., it can be provided as input to computer system 20). Insofar as ECG leads are well understood, and for the sake of clarity in the figures, the leads and their connections to computer 20 are not illustrated in FIG. 2.

A representative catheter 13 having at least one electrode 17 (e.g., a distal electrode) is also shown. This representative catheter electrode 17 is referred to as the "roving electrode," "moving electrode," or "measurement electrode" throughout the specification. Typically, multiple electrodes on catheter 13, or on multiple such catheters, will be used. In one embodiment, for example, the system 8 may comprise sixty-four electrodes on twelve catheters disposed within the heart and/or vasculature of the patient. Of course, this embodiment is merely exemplary, and any number of electrodes and catheters may be used.

Figure 3:
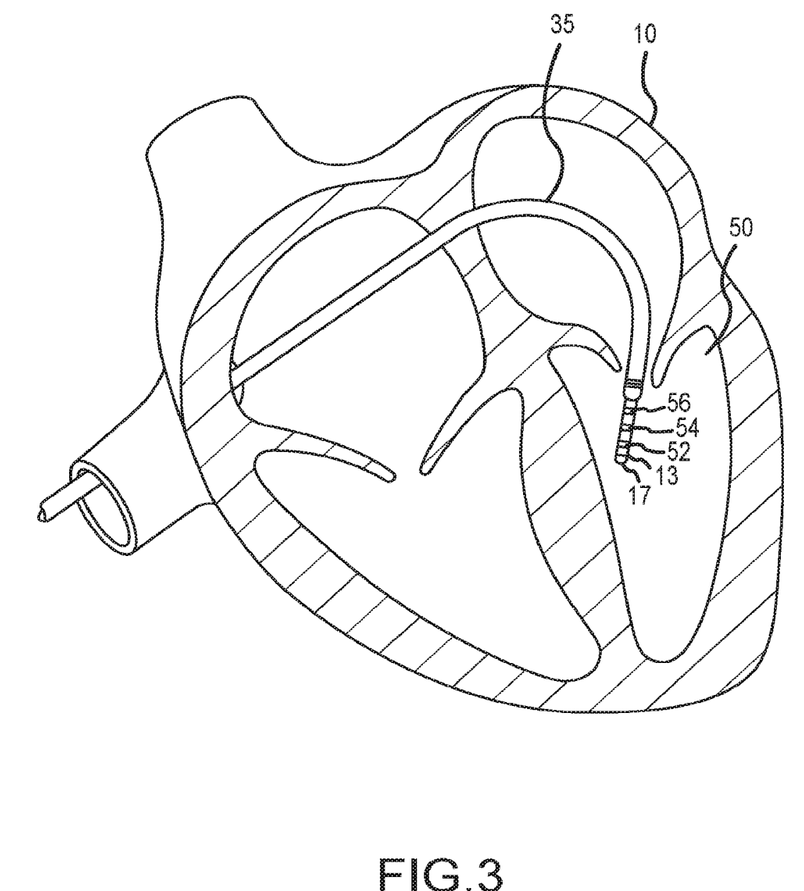
FIG. 3 depicts an exemplary catheter that can be used in an electrophysiology study.

Likewise, it should be understood that catheter 13 (or multiple such catheters) are typically introduced into the heart and/or vasculature of the patient via one or more introducers and using familiar procedures. For purposes of this disclosure, a segment of an exemplary multi-electrode catheter 13 is shown in FIG. 3. In FIG. 3, catheter 13 extends into the left ventricle 50 of the patient's heart 10 through a transseptal sheath 35. The use of a transseptal approach to the left ventricle is well known and will be familiar to those of ordinary skill in the art, and need not be further described herein. Of course, catheter 13 can also be introduced into the heart 10 in any other suitable manner.

Catheter 13 includes electrode 17 on its distal tip, as well as a plurality of additional measurement electrodes 52, 54, 56 spaced along its length in the illustrated embodiment. Typically, the spacing between adjacent electrodes will be known, though it should be understood that the electrodes may not be evenly spaced along catheter 13 or of equal size to each other. Since each of these electrodes 17, 52, 54, 56 lies within the patient, location data may be collected simultaneously for each of the electrodes by system 8.

Similarly, each of electrodes 17, 52, 54, and 56 can be used to gather electrophysiological data from the cardiac surface. The ordinarily skilled artisan will be familiar with various modalities for the acquisition and processing of electrophysiology data points (including, for example, both contact and non-contact electrophysiological mapping), such that further discussion thereof is not necessary to the understanding of the techniques disclosed herein. Likewise, various techniques familiar in the art can be used to generate a graphical representation from the plurality of electrophysiology data points. Insofar as the ordinarily skilled artisan will appreciate how to create electrophysiology maps from electrophysiology data points, the aspects thereof will only be described herein to the extent necessary to understand the instant disclosure.

Returning now to FIG. 2, in some embodiments, an optional fixed reference electrode 31 (e.g., attached to a wall of the heart 10) is shown on a second catheter 29. For calibration purposes, this electrode 31 may be stationary (e.g., attached to or near the wall of the heart) or disposed in a fixed spatial relationship with the roving electrodes (e.g., electrodes 17, 52, 54, 56), and thus may be referred to as a "navigational reference" or "local reference." The fixed reference electrode 31 may be used in addition or alternatively to the surface reference electrode 21 described above. In many instances, a coronary sinus electrode or other fixed electrode in the heart 10 can be used as a reference for measuring voltages and displacements; that is, as described below, fixed reference electrode 31 may define the origin of a coordinate system.

Each surface electrode is coupled to a multiplex switch 24, and the pairs of surface electrodes are selected by software running on a computer 20, which couples the surface electrodes to a signal generator 25. Alternately, switch 24 may be eliminated and multiple (e.g., three) instances of signal generator 25 may be provided, one for each measurement axis (that is, each surface electrode pairing).

The computer 20, for example, may comprise a conventional general-purpose computer, a special-purpose computer, a distributed computer, or any other type of computer. The computer 20 may comprise one or more processors 28, such as a single central processing unit (CPU), or a plurality of processing units, commonly referred to as a parallel processing environment, which may execute instructions to practice the various aspects described herein.

Generally, three nominally orthogonal electric fields are generated by a series of driven and sensed electric dipoles (e.g., surface electrode pairs 12/14, 18/19, and 16/22) in order to realize catheter navigation in a biological conductor. Alternatively, these orthogonal fields can be decomposed and any pairs of surface electrodes can be driven as dipoles to provide effective electrode triangulation. Likewise, the electrodes 12, 14, 18, 19, 16, and 22 (or any number of electrodes) could be positioned in any other effective arrangement for driving a current to or sensing a current from an electrode in the heart. For example, multiple electrodes could be placed on the back, sides, and/or belly of patient 11. Additionally, such non-orthogonal methodologies add to the flexibility of the system. For any desired axis, the potentials measured across the roving electrodes resulting from a predetermined set of drive (source-sink) configurations may be combined algebraically to yield the same effective potential as would be obtained by simply driving a uniform current along the orthogonal axes.

Thus, any two of the surface electrodes 12, 14, 16, 18, 19, 22 may be selected as a dipole source and drain with respect to a ground reference, such as belly patch 21, while the unexcited electrodes measure voltage with respect to the ground reference. The roving electrodes 17, 52, 54, 56 placed in the heart 10 are exposed to the field from a current pulse and are measured with respect to ground, such as belly patch 21. In practice the catheters within the heart 10 may contain more or fewer electrodes than the four shown, and each electrode potential may be measured. As previously noted, at least one electrode may be fixed to the interior surface of the heart to form a fixed reference electrode 31, which is also measured with respect to ground, such as belly patch 21, and which may be defined as the origin of the coordinate system relative to which localization system 8 measures positions. Data sets from each of the surface electrodes, the internal electrodes, and the virtual electrodes may all be used to determine the location of the roving electrodes 17, 52, 54, 56 within heart 10.

The measured voltages may be used by system 8 to determine the location in three-dimensional space of the electrodes inside the heart, such as roving electrodes 17, 52, 54, 56, relative to a reference location, such as reference electrode 31. That is, the voltages measured at reference electrode 31 may be used to define the origin of a coordinate system, while the voltages measured at roving electrodes 17, 52, 54, 56 may be used to express the location of roving electrodes 17, 52, 54, 56 relative to the origin. In some embodiments, the coordinate system is a three-dimensional (x, y, z) Cartesian coordinate system, although other coordinate systems, such as polar, spherical, and cylindrical coordinate systems, are contemplated.

As should be clear from the foregoing discussion, the data used to determine the location of the electrode(s) within the heart is measured while the surface electrode pairs impress an electric field on the heart. The electrode data may also be used to create a respiration compensation value used to improve the raw location data for the electrode locations as described, for example, in U.S. Pat. No. 7,263,397, which is hereby incorporated herein by reference in its entirety. The electrode data may also be used to compensate for changes in the impedance of the body of the patient as described, for example, in U.S. Pat. No. 7,885,707, which is also incorporated herein by reference in its entirety.

Therefore, in one representative embodiment, the system 8 first selects a set of surface electrodes and then drives them with current pulses. While the current pulses are being delivered, electrical activity, such as the voltages measured with at least one of the remaining surface electrodes and in vivo electrodes, is measured and stored. Compensation for artifacts, such as respiration and/or impedance shifting, may be performed as indicated above.

In some embodiments, system 8 is the EnSite™ Velocity™ cardiac mapping and visualization system of St. Jude Medical, Inc., which generates electrical fields as described above, or another localization system that relies upon electrical fields. Other localization systems, however, may be used in connection with the present teachings, including for example, systems that utilize magnetic fields instead of or in addition to electrical fields for localization. Examples of such systems include, without limitation, the CARTO navigation and location system of Biosense Webster, Inc., the AURORA® system of Northern Digital Inc., Sterotaxis' NIOBE® Magnetic Navigation System, as well as MediGuide™ Technology and the EnSite™ Precision™ system, both from St. Jude Medical, Inc.

The localization and mapping systems described in the following patents (all of which are hereby incorporated by reference in their entireties) can also be used with the present invention: U.S. Pat. Nos. 6,990,370; 6,978,168; 6,947,785; 6,939,309; 6,728,562; 6,640,119; 5,983,126; and 5,697,377.

The system 8 further includes a LAVA detection and analysis module 58 that can be used to analyze one or more metrics associate with late activations, including the probability of an EGM signal containing a LAVA, and a computation of the lateness associated with the activation. Based on this information, and as discussed further herein, these metrics can be used to generate various maps that can be displayed on a display screen for further analysis by the physician.

Figure 4:
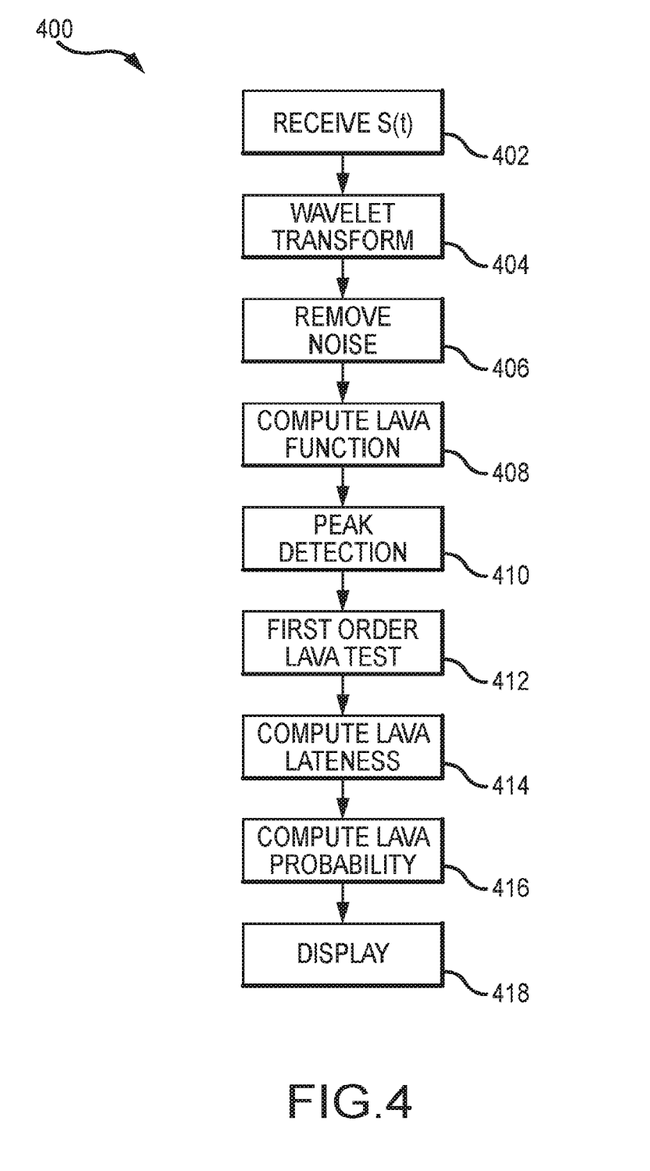
FIG. 4 is a flowchart of representative steps that can be followed according to exemplary embodiments disclosed herein.

One exemplary method for detecting the presence of a LAVA within an EGM signal will be explained herein with reference to the flowchart 400 of representative steps presented as FIG. 4. In some embodiments, for example, flowchart 400 may represent several exemplary steps that can be carried out by the computer 20 of FIG. 2 (e.g., by processor 28, including LAVA detection and analysis module 58). It should be understood that the representative steps described below can be either hardware- or software-implemented. For the sake of explanation, the term "signal processor" is used herein to describe both hardware- and software-based implementations of the teachings herein.

In step 402, an electrogram signal, denoted S(t) (and illustrated as trace 502 in panel A of FIG. 5), is received at a signal processor (e.g., by one or more processors 28 within computer 20, including LAVA detection and analysis module 58). According to aspects of the disclosure, the electrogram signal S(t) is a bipolar signal (e.g., a bipolar EGM received from catheter 13 in FIG. 3). It is contemplated, however, that the teachings herein can also be applied to unipolar electrogram signals and/or to monophasic action potential ("MAP") signals.

Figure 5:
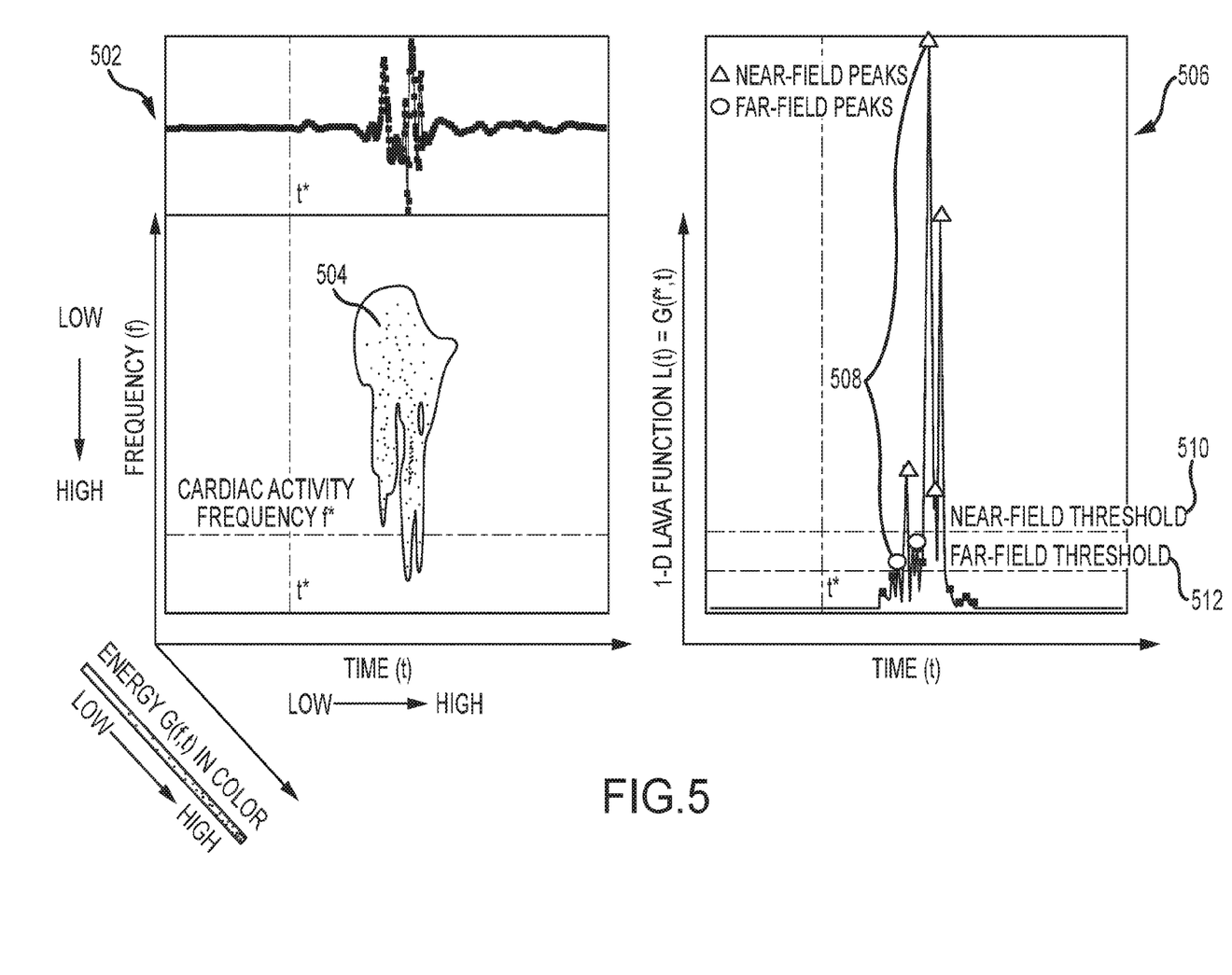
FIG. 5 is a view showing an exemplary bipolar electrogram analyzed within an RAI and its corresponding continuous wavelet transformation scalogram and LAVA function.

In block 404, the electrogram signal S(t) is transformed into the wavelet domain, which computes a scalogram G(f, t) (illustrated as scalogram 504 in panel B of FIG. 5). More specifically, G(f, t) can be computed for a preset window, referred to herein as a "Roving Activation Interval" ("RAI") about a reference time point, referred to herein as $T_{ref}$. According to aspects disclosed herein, $T_{ref}$ corresponds to QRS activity detected using a user-defined reference cardiac signal, such as the signal from an EKG lead or the signal from an in vivo reference electrode (e.g., electrode 31, which can be positioned within the coronary sinus).

Likewise, the width of the RAI can be user defined. According to aspects of the disclosure, the RAI is between about 100 ms and about 300 ms wide.

For purposes of illustration, the figures herein are displayed in the full width of an exemplary RAI centered about an exemplary $T_{ref}$.

In embodiments, block 404 applies a continuous wavelet transform to the electrogram signal S(t). A continuous wavelet transform provides a very redundant, but also very finely detailed, description of a signal in terms of both time and frequency. Continuous wavelet transforms are particularly helpful in tackling problems involving signal identification and detection of hidden transients (e.g., hard to detect, short-lived elements of a signal).

The mother wavelet used in the wavelet transform can be a high time-resolution mother wavelet, such as a Paul wavelet, or a high frequency-resolution mother wavelet, such as a Morlet wavelet, both of which will be familiar to those of ordinary skill in the art. Of course, other mother wavelets can also be employed without departing from the scope of the instant teachings. The teachings herein can also be applied using discrete wavelet transforms.

If desired, noise can be removed from the scalogram G(f, t) in block 406. For example, the energy amplitudes within the RAI can be normalized to values between 0 and 1, with the highest energy amplitude within the RAI corresponding to 1. Once the energy amplitudes have been so normalized, values of G(f, t) less than a preset, and optionally user-defined, noise threshold, such as about 0.2, can be set to zero, and thus eliminated from the scalogram G(f, t).

As discussed in greater detail below, for each cardiac trigger, the electrogram signal S(t) within the RAI is analyzed to detect various near-field and far-field peaks. In block 408, a one-dimensional LAVA function L(t) is computed of the scalogram G(f, t). The LAVA function can be of form L(t)=G(f*, t), where is a preset, and optionally user-defined, cardiac activity frequency, such as about 300 Hz. Panel C of FIG. 5 depicts the LAVA function 506 that corresponds to electrogram signal 502 and associated scalogram 504.

In other embodiments, the LAVA function can be of form $L(t)=f_{max}(t)$, where $f_{max}$ is defined as the maximum frequency at a time t, with $G(f_{max}, t)>0$.

In block 410, one or more peaks are detected in the LAVA function L(t). In embodiments, a first order analysis detects all local maximum peaks in the LAVA function L(t).

The detected local maximum peaks are then analyzed to determine whether they are dominant activity peaks. According to aspects of this disclosure, a local maximum peak qualifies as a dominant activity peak if the maximum value of the slope of the electrogram signal S(t), within a preset refractory window about the local maximum peak, exceeds a preset, and optionally user-defined, discrete activity threshold.

The slope of the electrogram signal S(t) can be computed as a first derivative S'(t) of the electrogram signal S(t). In embodiments of the disclosure, the first derivative can be computed as $$S'(t) = \frac{S(t+\Delta T) - S(t)}{\Delta T},$$

where ΔT is a preset time interval, such as about 3 ms.

The refractory window, within which the maximum slope of the electrogram signal S(t) is analyzed, can be about 2.5 ms to either side of the local maximum peak.

The discrete activity threshold can be about 0.2 mV/msec.

Panel C of FIG. 5 depicts a plurality of dominant activity peaks (for the sake of clarity, only two are shown with lead lines from reference numeral 508) in LAVA function 506, each of which can be categorized as a near-field peak (represented by a triangular icon), a far-field peak (represented by a circular icon), or a noise peak (not represented by any special icon). In embodiments, the following logic is used to categorize dominant activity peaks:

If L(t) at the dominant activity peak exceeds a preset, and optionally user-defined, near-field threshold (510), then the peak can be categorized as a near-field peak;

If L(t) at the dominant activity peak exceeds a preset, and optionally user-defined, far-field threshold (512), but not the near-field threshold (510) described above, then the peak can be categorized as a far-field peak; and If L(t) at the dominant activity peak does not exceed the far-field threshold (512) described above, then the peak can be categorized as a noise peak and discarded.

In some embodiments, the preset far-field threshold (512) is about 2.5 times the length of the electrogram signal S(t) and the preset near-field threshold (510) is about 5 times the length of the electrogram signal S(t).

In block 412, a first order analysis for LAVAs is applied to the electrogram signal S(t). According to aspects of the disclosure, this first order test compares the peak-to-peak amplitude of the electrogram signal S(t) to a preset, and optionally user-defined, amplitude threshold, such as about 5 mV. If the peak-to-peak amplitude of the electrogram signal S(t) does exceed the amplitude threshold, then the electrogram S(t) is likely coming from healthy tissue. If, on the other hand, the peak-to-peak amplitude of the electrogram signal S(t) does not exceed the amplitude threshold, then further LAVA analysis as described herein can be conducted In block 414, a LAVA lateness parameter is computed for the electrogram signal S(t) using one of the LAVA function peaks detected in block 410. According to aspects of the disclosure, the LAVA lateness parameter is computed as a time difference between either the latest in time near-field peak detected in the LAVA function L(t) or the latest in time far-field peak detected in the LAVA function L(t), on the one hand, and a reference ECG QRS signal, on the other hand. More particularly, the latest in time near-field peak is used to compute the LAVA lateness parameter if any near-field peaks are detected in the LAVA function; otherwise, the latest in time far-field peak is used to compute the LAVA lateness parameter.

In block 416, a LAVA probability parameter is computed for the electrogram signal S(t). The LAVA probability parameter can take into consideration the LAVA lateness parameter for the electrogram signal S(t), a fractionation parameter for the electrogram signal S(t), a total number of peaks detected in the LAVA function L(t), a number of far-field peaks detected in the LAVA function L(t), a near field activity width, a number of isolated QRS activities, and/or a QRS activity duration for the electrogram signal S(t). The LAVA probability parameter, the number of peaks, and the number of far-field peaks are all described above. One of ordinary skill in the art will be familiar with the computation of near field activity widths and the identification of QRS activities. The fractionation parameter and QRS activity duration are described below.

Fractionation Parameter. The fractionation parameter is a measure of the fractionation of electrogram signal S(t). In embodiments of the disclosure, the fractionation parameter is computed as the number of times the slope of the electrogram signal S(t) (or a noise-filtered version of the electrogram signal, denoted S*(t)) changes sign between the earliest in time near-field peak detected in the LAVA function L(t) and the latest in time near-field peak detected in the LAVA function L(t).

By way of further explanation, a first step in computing the fractionation parameter can be to remove noise from the electrogram signal S(t) (that is, to generate S*(t)). To generate S*(t), the LAVA function L(t) (which has had noise removed therefrom as described above in connection with the discussion of scalogram G(f, t)) can be converted into a pulse wave $L^{Pulse}(t)$ where $$L^{Pulse}(t) = \begin{cases} 1, & \text{if } L(t) > 0 \\ 0, & \text{otherwise} \end{cases}.$$

can then be multiplied by S(t) to generate S*(t).

Once S*(t) is generated, the slope thereof can be analyzed between the earliest in time near-field peak detected in the LAVA function L(t) and the latest in time near-field peak detected in the LAVA function L(t). According to aspects of the disclosure, the slope can be defined as $$\frac{S*(t+\Delta T) - S*(t)}{\Delta T},$$

where $\Delta T$ can be based on the sampling rate of system 8 (e.g., about 0.5 ms in the case of the EnSite™ Velocity™ system). As described above, the number of fluctuations (that is, sign changes) in the slope of S*(t) that occur between the earliest in time near-field peak detected in the LAVA function L(t) and the latest in time near-field peak detected in the LAVA function L(t) can be set as the fractionation parameter.

QRS Activity Duration. The QRS activity duration for the electrogram signal S(t) can be computed using the near- and far-field peaks detected in the LAVA function. In some embodiments of the disclosure, the QRS activity duration can be computed using the earliest and latest in time near-field peaks detected in the LAVA function (denoted $t_{first}^{NF}$ and $t_{last}^{NF}$, respectively) and the earliest and latest in time far-field peaks detected in the LAVA function (denoted $t_{first}^{FF}$ and $t_{last}^{FF}$, respectively), as follows:

$$QRS \text{ Activity Duration} = \begin{cases} t_{last}^{NF} - t_{first}^{NF}, & \text{if } t_{first}^{NF} < t_{first}^{FF} \text{ and } t_{last}^{NF} > t_{last}^{FF} \\ t_{last}^{FF} - t_{first}^{FF}, & \text{if } t_{first}^{FF} < t_{first}^{NF} \text{ and } t_{last}^{FF} > t_{last}^{NF} \\ t_{last}^{NF} - t_{first}^{FF}, & \text{if } t_{first}^{FF} < t_{first}^{NF} \text{ and } t_{last}^{NF} > t_{last}^{FF} \\ t_{last}^{FF} - t_{first}^{NF}, & \text{if } t_{first}^{NF} < t_{first}^{FF} \text{ and } t_{last}^{FF} > t_{last}^{NF} \end{cases}.$$

The overall LAVA probability parameter can be computed as a weighted value based upon one or more of the parameters described above. According to aspects of the disclosure, the LAVA probability parameter is a cumulative weighted value, which can computed as shown in exemplary Table 1 and/or exemplary Table 2, where a subsequent step is only taken if the previous step did not cause the LAVA probability to exceed 100%.

TABLE 1

Exemplary Steps for Computing LAVA Probability

| STEP | PARAMETER | CONDITION | WEIGHT |
|---|---|---|---|
| 1 | Lateness Parameter | 30 ms-50 ms | Linear grade from 30% to 100% |
| 2 | Fractionation Parameter | >3 | 60% |
| 3 | Number of Peaks | Total peaks >10 | 10% |

TABLE 1-continued

Exemplary Steps for Computing LAVA Probability

| STEP | PARAMETER | CONDITION | WEIGHT |
|---|---|---|---|
| | | OR Near-field peaks ≥3 | |
| 4 | Number of Far Field Peaks | ≥3 | 5% |
| 5 | QRS Activity Duration | >15 ms | 5% |

TABLE 2

Exemplary Steps for Computing LAVA Probability

| STEP | PARAMETER | CONDITION | WEIGHT |
|---|---|---|---|
| 1 | Lateness Parameter | 30 ms-50 ms | Linear grade from 0% to 100% |
| 2 | Fractionation Parameter | 3 to 5 sign changes | Linear grade from 0% to 25% |
| 3 | Number of Peaks | 3 to 5 total peaks | Linear grade from 0% to 25% |
| 4 | Near Field Activity Width | 15-75 ms | Linear grade from 0% to 75% |
| 5 | Number of Isolated QRS Activities | 2-5 | Linear grade from 0% to 75% |
| 5 | QRS Activity Duration | 15-75 ms | Linear grade from 0% to 75% |

Once the LAVA lateness and LAVA probability parameters have been computed, they can be displayed in block 418. For example, they can be provided to a user as numerical values on a display screen (e.g., as an annotation or note displayed alongside the electrogram signal that produced the LAVA. The parameters can also be saved for future analysis (e.g., for subsequent review or off-line analysis). During electrophysiology studies, these metrics can be used to grade the vast range of early to late LAVAs observed, allowing a physician to determine whether to perform additional diagnostic and/or therapeutic actions. In some cases, for example, surviving fibers in a scar can be detected as high frequency signals occurring any time during or after the far-field electrogram (LAVAs).

Figure 6:
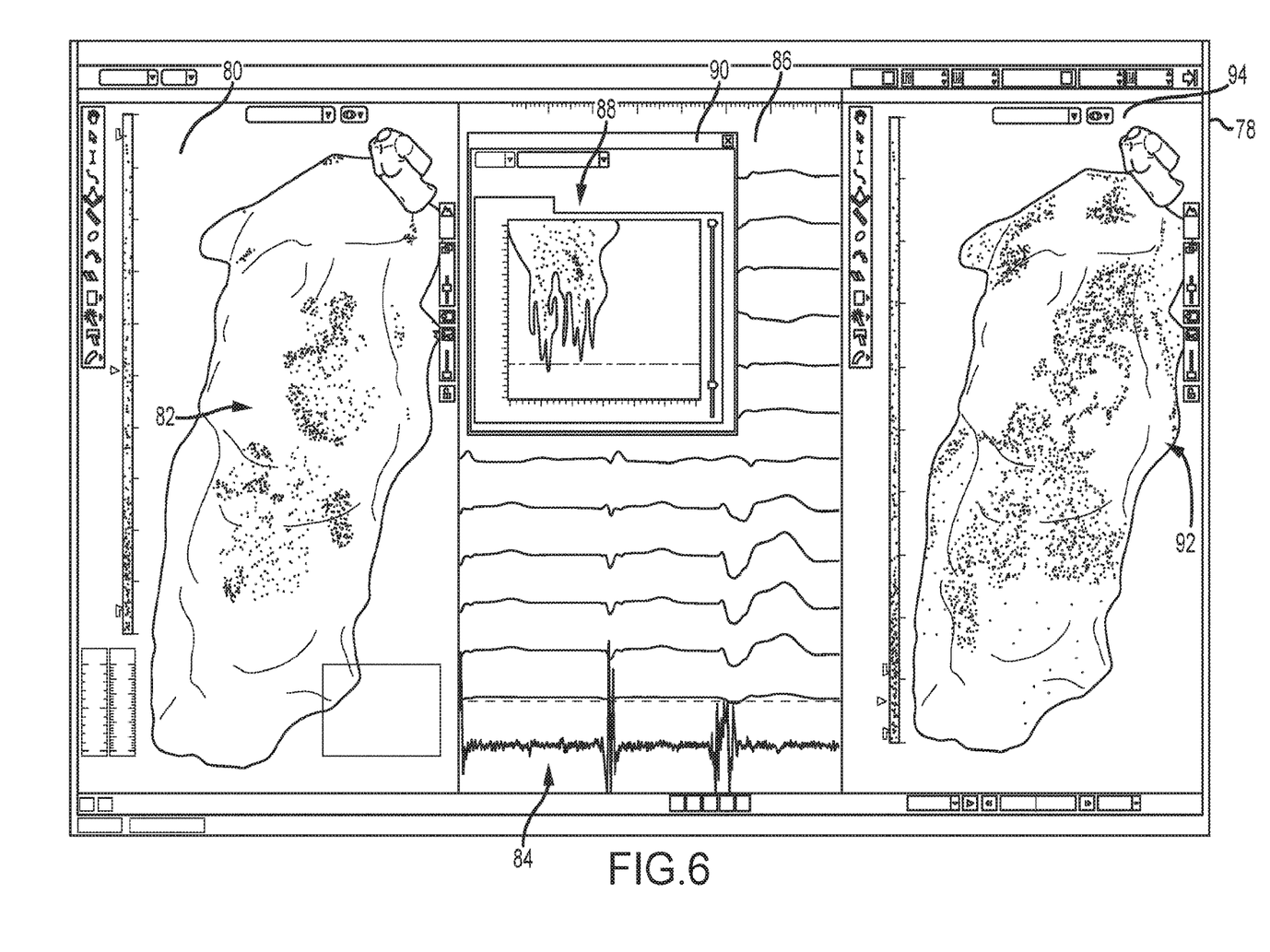
FIG. 6 is an exemplary display screen showing a LAVA probability map, the specific bipolar electrogram under analysis, a representation of the 1-D LAVA function associated with the bipolar electrogram, and a peak-to-peak voltage map.

In some embodiments, and as can be further seen in FIG. 6, the system 8 is configured to generate one or more maps using the computed LAVA lateness and/or probability parameters. FIG. 6 may represent an exemplary display screen 78 generated by system 8, wherein a first pane 80 of the screen 78 shows a sample LAVA probability map 82 (in %) with different colors on the map 82 representing different percentage LAVA probability values (e.g., red/orange colors represent relatively high LAVA probability values whereas blue/violet colors represent relatively low LAVA probability values). The specific bipolar EGM signal 84 that is being analyzed can also be displayed in a second pane 86 on the display screen 78. The LAVA function 88 that was used in the LAVA computation can also be displayed in a third pane 90 on the display screen 78. Other maps, such as peak-to-peak voltage map 92, may also be displayed on other panes 94, as shown. As described above, various techniques familiar in the art can be used to generate a graphical representation from a plurality of electrophysiology data points, including the parameters described herein, such that a detailed discussion of the creation of the foregoing maps is not necessary to an understanding of the present disclosure.

Figure 7:
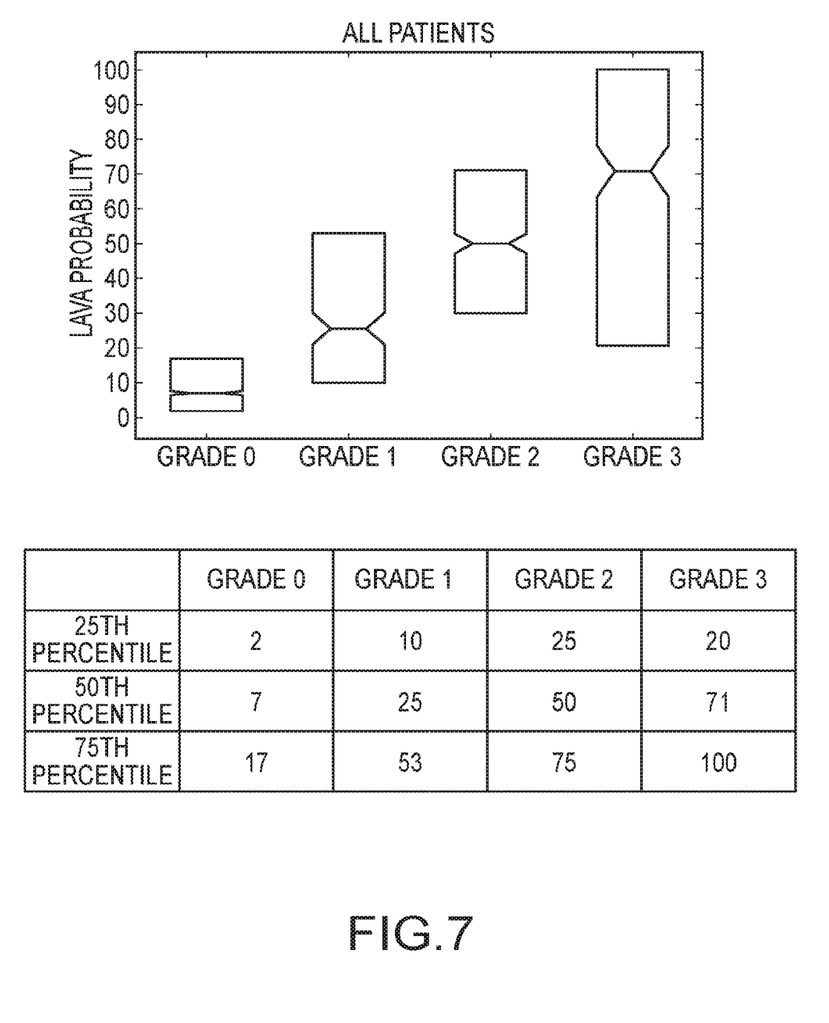
FIG. 7 shows the relationship between LAVA probability parameter values and LAVA grades in both box plot and tabular formats.
Figure 8:
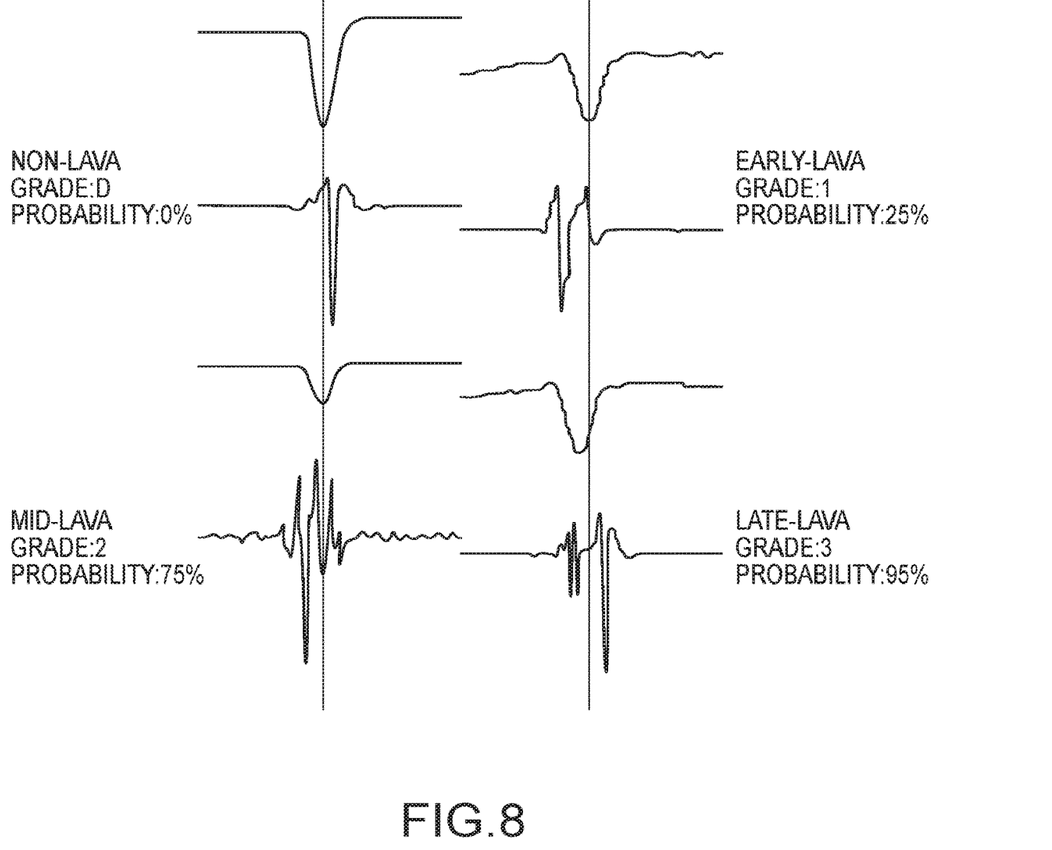
FIG. 8 shows several exemplary plots of electrogram waveforms containing non-LAVA and LAVA potentials.
Figure 9:
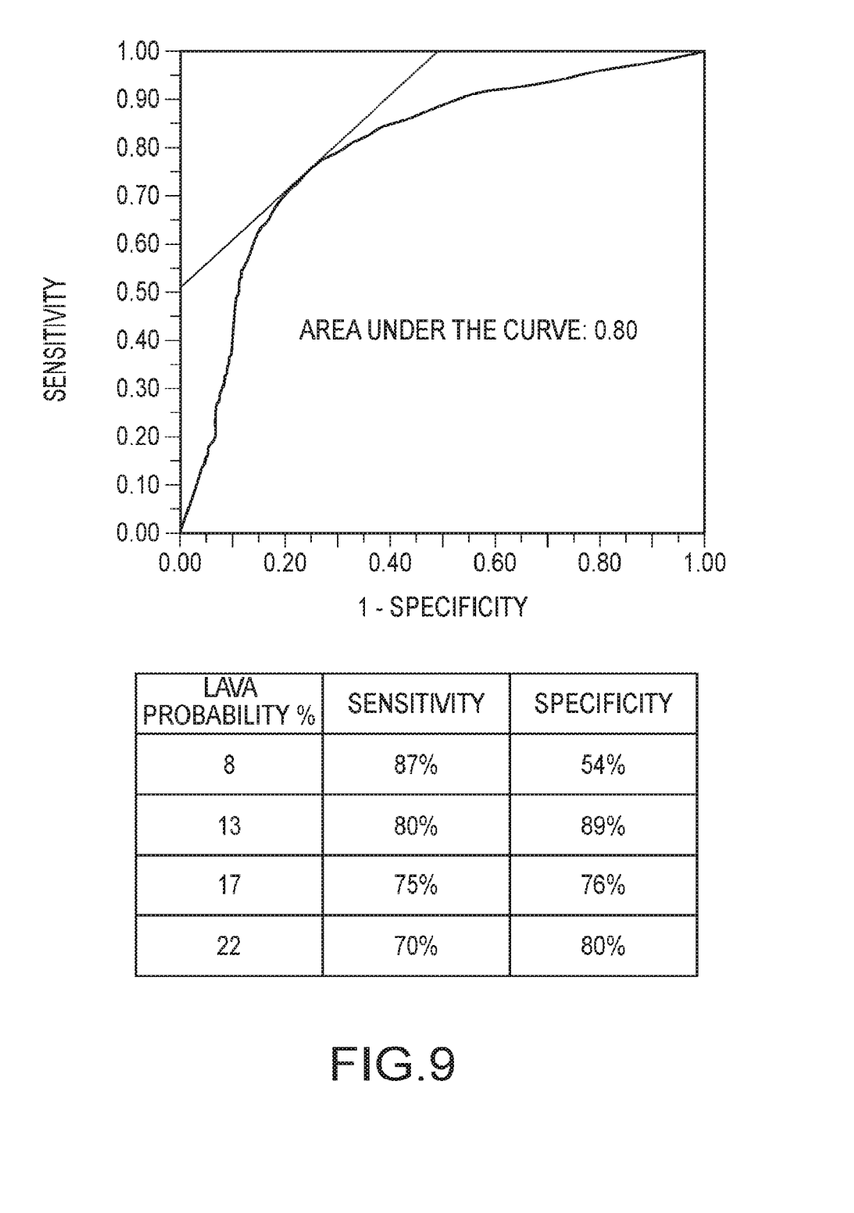
FIG. 9 depicts an ROC curve for various cutoff levels of LAVA probability parameter values for non-LAVA vs LAVA.

FIGS. 7-9 illustrate validation of the foregoing teachings using statistical analysis and the categorization of electrogram signals into different grades by experienced practitioners. As can be seen in the plot at the upper portion of FIG.

7, for example, a number of contact electrograms (exemplary waveforms are shown in FIG. 8) were analyzed and categorized by practitioners according to the following exemplary grading scheme:

Grade 0: Non-LAVAs/Healthy potentials;
Grade 1: Early diastolic LAVAs with fused multiple potentials;
Grade 2: Mid diastolic LAVAs with fragmented potentials;
Grade 3: Late diastolic LAVAs with late potentials; and
Noise.

FIG. 7 also shows, both in box-plot and numerical form, the distribution of LAVA probabilities, as computed by system 8 according to the teachings herein, for each grade.

FIG. 9 depicts an exemplary ROC curve for various cutoff levels of LAVA probability parameter for non-LAVA vs LAVA. The ROC curve graphically displays the trade-off between sensitivity and specificity of LAVA identification and assigns an optimal cut-off, such as 18%, as shown. As can be understood from both FIGS. 7 and 9, mostly late— (Grade 3) or mid-diastolic (Grade 2) LAVAs were observed at 70% LAVA probability or higher, whereas early diastolic LAVAs (Grade 1) had relatively lower probabilities. Such information can be used by the physician as feedback to determine which sites are good candidate sites for ablation.

The LAVA probability parameters for the different graded signals can be analyzed for agreement using a statistical approach. The LAVA probability parameters can also be compared visually against a LAVA probability map to determine visual agreement between the computed probabilities and the area(s) within the LAVA probability map having higher values around the location of ablation lesions and/or other locations tagged during a study.

Although several embodiments have been described above with a certain degree of particularity, those skilled in the art could make numerous alterations to the disclosed embodiments without departing from the spirit or scope of this invention.

For example, although the foregoing describes a representative process occurring in real time (e.g., processing electrograms as they are received from an in vivo catheter), the teachings herein are equally applicable during post-processing (e.g., processing a previously-collected set of electrograms).

All directional references (e.g., upper, lower, upward, downward, left, right, leftward, rightward, top, bottom, above, below, vertical, horizontal, clockwise, and counter-clockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A method of analyzing cardiac activity for local abnormal ventricular activity (LAVA), comprising:
   receiving an electrogram signal at a signal processor; and
   using the signal processor:
      transforming the electrogram signal into the wavelet domain, thereby computing a scalogram;
      computing a one-dimensional LAVA function of the scalogram;
      detecting one or more peaks in the LAVA function;
      computing a peak-to-peak amplitude of the electrogram signal, and, if the peak-to-peak amplitude does not exceed a preset amplitude threshold:
         computing a LAVA lateness parameter for the electrogram signal using one of the one or more peaks detected in the LAVA function; and
         computing a LAVA probability parameter for the electrogram signal.

2. The method according to claim 1, wherein transforming the electrogram signal into the wavelet domain comprises applying a continuous wavelet transformation to the electrogram signal to compute the scalogram.

3. The method according to claim 1, further comprising setting values of the scalogram less than a preset noise threshold to zero.

4. The method according to claim 1, wherein computing a one-dimensional LAVA function of the scalogram comprises computing a one-dimensional LAVA function of the scalogram at a preset cardiac activity frequency.

5. The method according to claim 4, wherein the preset cardiac activity frequency is 300 Hz.

6. The method according to claim 1, wherein detecting one or more peaks in the LAVA function comprises:
   detecting one or more dominant activity peaks in the LAVA function;
   categorizing each dominant activity peak of one or more dominant activity peaks as a near-field peak, a far-field peak, or a noise peak.

7. The method according to claim 6, wherein detecting a plurality of dominant activity peaks in the LAVA function comprises detecting one or more local maximum peaks in the LAVA function where a maximum value of a slope of the electrogram signal exceeds a preset discrete activity threshold within a preset refractory window surrounding the local maximum peak.

8. The method according to claim 7, wherein the preset discrete activity threshold is 0.2 mV/msec.

9. The method according to claim 6, wherein categorizing each dominant activity peak of one or more dominant activity peaks as a near-field peak, a far-field peak, or a noise peak comprises:
   categorizing a dominant activity peak as a near-field peak if the LAVA function exceeds a preset near field threshold at the dominant activity peak;
   categorizing the dominant activity peak as a far-field peak if the LAVA function exceeds a preset far field threshold and not the preset near field threshold at the dominant activity peak; and
   categorizing the dominant activity peak as a noise peak otherwise.

10. The method according to claim 1, wherein computing a LAVA lateness parameter for the electrogram signal using one of the one or more peaks detected in the LAVA function comprises computing the LAVA lateness parameter as a time difference between:
   a latest far-field peak of the one or more peaks detected in the LAVA function and a reference ECG QRS, if the one or more peaks detected in the LAVA function do not include any near-field peaks; and
   a latest near-field peak of the one or more peaks detected in the LAVA function and the reference ECG QRS if the one or more peaks detected in the LAVA function do include at least one near-field peak.

11. The method according to claim 1, wherein computing a LAVA probability parameter for the electrogram signal comprises computing a LAVA probability parameter using one or more of: the LAVA lateness parameter for the electrogram signal; a fractionation parameter for the electrogram signal; a number of peaks detected in the LAVA function; a number of far-field peaks detected in the LAVA function; a near field activity span for the electrogram signal; a number of isolated QRS activities for the electrogram signal; and a QRS activity duration for the electrogram signal.

12. The method according to claim 11, wherein the fractionation parameter for the electrogram signal is computed as a number of sign changes in a slope of the electrogram signal between an earliest near-field peak detected in the LAVA function and a latest near-field peak detected in the LAVA function.

13. The method according to claim 11, wherein the fractionation parameter for the electrogram signal is computed as a number of sign changes in a slope of the electrogram signal, after the electrogram signal has been filtered to remove noise, between an earliest near-field peak detected in the LAVA function and a latest near-field peak detected in the LAVA function.

14. The method according to claim 11, wherein the QRS activity duration for the electrogram signal is computed using the one or more peaks detected in the LAVA function.

15. A method of analyzing a cardiac electrogram for local abnormal ventricular activity (LAVA) in an electroanatomical mapping system, the method comprising the electroanatomical mapping system:
transforming the cardiac electrogram into the wavelet domain, thereby computing a scalogram;
computing a one-dimensional LAVA function of the scalogram;
detecting one or more peaks in the LAVA function;
computing a peak-to-peak amplitude of the electrogram signal, and, if the peak-to-peak amplitude does not exceed a preset amplitude threshold, computing at least one of:
a LAVA lateness parameter for the electrogram signal using one of the one or more peaks detected in the LAVA function; and
a LAVA probability parameter for the electrogram signal.

16. The method according to claim 15, wherein detecting one or more peaks in the LAVA function comprises detecting one or more local maximum peaks in the LAVA function where:
a maximum value of a slope of the electrogram signal exceeds a preset discrete activity threshold within a preset refractory window surrounding the local maximum peak; and
the LAVA function exceeds at least a preset far field threshold at the local maximum peak.

17. An electroanatomical mapping system configured to analyze an electrogram signal for local abnormal ventricular activity (LAVA), the electroanatomical mapping system comprising:
a LAVA analysis processor configured to:
transform the electrogram signal into the wavelet domain, thereby computing a scalogram;
compute a one-dimensional LAVA function of the scalogram;
detect one or more peaks in the LAVA function; and
compute one or more of a LAVA lateness parameter for the electrogram signal using one of the one or more peaks detected in the LAVA function and a LAVA probability parameter for the electrogram signal.

18. The electroanatomical mapping system according to claim 17, wherein the LAVA analysis processor is configured to compute the one or more of the LAVA lateness parameter and the LAVA probability parameter when a peak-to-peak amplitude of the electrogram signal does not exceed a preset amplitude threshold.

* * * * *